United States Patent [19]

Gaede et al.

[11] Patent Number: 4,948,902

[45] Date of Patent: Aug. 14, 1990

[54] PROCESS FOR MAKING SUBSTITUTED PYRAZOLES

[75] Inventors: Bruce J. Gaede, University City; Lisa L. Torrence, Herculaneum, both of Mo.

[73] Assignee: Monsanto Company, St. Louis, Mo.

[21] Appl. No.: 175,462

[22] Filed: Apr. 13, 1988

[51] Int. Cl.$^5$ .............................. C07D 231/46
[52] U.S. Cl. .................................... 548/376
[58] Field of Search .................. 548/375, 376, 378

[56] References Cited

U.S. PATENT DOCUMENTS 4,099,012 7/1978 Gschwend .................... 548/378
4,245,106 1/1981 Brannigan et al. ............ 548/378

OTHER PUBLICATIONS

Liljefors et al., Acta. Chem. Scand. 24, pp. 3109–3115(1970).
March, J., "Advanced Organic Chemistry", 3rd ed. (1985), p. 375.
Ibrahim et al., "Heterocyoles" 24 pp. 2085 (1986).
Mitteilung et al., Monatshefte for Chemie 112, pp. 875–877 (1981).
Nobuo et al., Chem. Abstracts 83, p. 121 (1975).
Gavrilenko et al., Zh. Org. Khim. 10 pp. 601–604. (1974).
Strakov et al., Chem. Abstracts, 80, p. 355 (1974).
Chem. Abstracts 94, 103400a (1981).
Schemore et al., J. Heterocyclic Chem. 19, p. 1355 (1982).
Auwers et al., Chem. Ber. 59, p. 1043–1055 (1926).
Menozzi et al., J. Heterocyclic Chem. 21, pp. 1437–1440 (1984).
Plath et al., Synthesis pp. 318–320 (1982).
Deshayes et al., J. Heterocyclic Chem. 21, pp. 301–304, (1984).
Beck et al., J. Heterocyclic Chem. pp. 739–740 (May--Jun. 1987).

*Primary Examiner*—John M. Ford
*Attorney, Agent, or Firm*—Stanley M. Tarter; Howard C. Stanley; Arnold H. Cole

[57] ABSTRACT

The present invention relates to a novel process for making N-alkyl-3-hydroxypyrazoles.

8 Claims, No Drawings

PROCESS FOR MAKING SUBSTITUTED PYRAZOLES

FIELD OF THE INVENTION

The present invention relates to a novel process for making N-alkyl-3-hydroxypyrazoles.

Background of the Invention

N-substituted hydroxypyrazoles and processes for their manufacture are known in the art, e.g., U.S. Pat. Nos. 4,382,948 and 4,557,753. These methods for making N-substituted hydroxypyrazoles result in the formation of N-substituted-5-hydroxypyrazoles. There is a need in the art for an efficient process for making N-alkyl-3-hydroxypyrazoles.

SUMMARY OF THE INVENTION

The present invention is an efficient process for preparing N-alkyl-3-hydroxypyrazoles which comprises reacting a 3-(amino or substituted amino)-2-alkenoic acid or acid derivative with an alkyl substituted hydrazine. The alkyl substituents on the hydrazine may in turn be substituted by a variety of other substituents, such as halo substituents. The alkenoic acid or acid derivative may also be substituted by a variety of substituents known to those skilled in the art. Suitable alkenoic acid derivatives included esters, thioesters and amides.

The 3-hydroxypyrazoles formed in the process of the present invention are useful as intermediates in making active herbicidal phenoxypyrazoles.

A more thorough disclosure of the present invention is presented in the detailed description which follows.

DETAILED DESCRIPTION

An illustrative embodiment of the present invention relates to a process for preparing a compound having the formula:

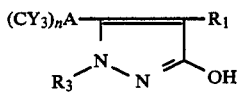

which comprises reacting

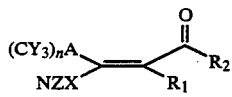

with $R_3NHNH_2$
wherein each Y is independently hydrido or halo; n is 0 or 1; A is $CFY_2$ when n is 0 and A is $CFY$ when n is 1; Z is hydrido and X is hydrido, lower alkyl, or phenyl, or Z and X together are cyclic alkyl; $R_1$ is hydrido or halo; $R_2$ is hydroxy, alkoxy, alkylthio or alkylamino; and $R_3$ is lower alkyl.

Y as halo is preferably a fluoro. Preferably, the substitient on the 3-position of the alkenoic acid is a $CY_3CF_2$— and more preferably the substituent is $CF_2Y$— as a difluoromethyl or trifluoromethyl. $R_2$ is preferably lower alkoxy, lower alkylthio or lower alkylamino. $R_3$ is preferably methyl. Z, X and $R_1$ are preferably hydrido.

The term "alkyl" means herein saturated straight or branched chain radicals having 1 to 6 carbon atoms. The term "lower alkyl" means alkyl having 1 to 2 carbon atoms. X and Z together as cyclicalkyl mean "—$CH_2(CH_2)_n$—$CH_2$—".

The term "hydrido" means a H—.

The term "halo" means herein a halogen radical preferably selected from bromo, chloro or fluoro and more preferably fluoro.

In the process of the present invention $R_1$ can be a variety of substituents known to those skilled in the art. The nature of the $R_1$ substituent is not important in the practice of the process of the present invention provided that it does not unduly interfere with the process of the present invention and does not unacceptably interact with solvents or reactants employed in the process. The use of reactants with other $R_1$ substituents is contemplated as equivalent to the process of the present invention. Further, $R_3$ can be substituted by a variety of non-interfering substituents known to those skilled in the art such as halo. The nature of such non-interfering substituents is not important in the practice of the process of the present invention provided that they do not unduly interfere with the process of the present invention or unacceptably interact with solvents or reactants employed in the process. The use of a reactant having an $R_3$ with such a non-interfering substituent is contemplated as equivalent to the process of the present invention.

Further, X as alkyl and phenyl and Z and X as cyclic alkyl can be substituted by non-interfering substituents known to those skilled in the art such as halo, nitro, hydroxy, and the like and the use of a reactant with such non-interfering substituents is contemplated as equivalent to the process of the present invention. Generally, more sterically hindered amines such as diethylamine and morpholine result in side reactions without product formation.

The starting 2-alkenoic acid derivatives and substituted hydrazines are known in the art, readily prepared by standard laboratory procedures or commercially available.

The starting material, a substituted 3-amino-2-butenoic ester, can be formed by addition of ammonia or amine to the corresponding substituted 3-oxobutanoic ester which optionally may be dissolved in a suitable solvent such as cyclohexane, methylcyclohexane, toluene or benzene. A preferred starting material in the process of the present invention, 3-amino-4,4,4-trifluoro-2-butenoic acid ester, can be formed by bubbling ammonia through trifluoroacetoacetate at elevated temperature of about 70° C. to 100° C. for a period of time of about 3 hours. Preferably, the reaction is run with stirring under ammonia pressure of about 50 psig.

Other types of acid derivatives can be formed by converting the corresponding 3-amino-alkenoic acid or alkenoic ester to the desired derivative using standard laboratory procedures or by forming the 3-aminoalkenoic acid derivative from the corresponding beta-keto acid derivative prior to amination. The process for making other acid derivatives will be known to those skilled in the art.

To form the 3-hydroxypyrazole, the 3-amino-2-alkenoic acid derivative can be reacted neat with the substituted hydrazines. Optionally, the reactants can be dissolved in suitable solvents such as methanol, methylcyclohexane, toluene, cyclohexane or benzene. The reaction is generally run at temperatures from about 0° to about 200° C. preferably about 60° to about 100° C.

for a period of about 1 to about 24 hours. The reaction will result in forming the corresponding 3-hydroxypyrazole as the product with some amount of 5-hydroxypyrazole present.

The 3- and 5-hydroxypyrazole isomers can be separated by standard laboratory procedures. The 3-hydroxypyrazole isomer can be separated out of the basic reaction mixture by acidifying the mixture to a pH of about 6 to 7 to precipitate the 3-hydroxypyrazole isomer from the mixture while the 5-hydroxypyrazole isomer remains in solution. The separation can also be accomplished by isolating the mixture of isomers from the reaction medium and adding the mixture of isomers to an aqueous solution of sodium bicarbonate. The 5-hydroxy isomer is dissolved into solution while the 3-hydroxy isomer remains in suspension and is readily separated. Alternatively, the 3-hydroxy isomer may be obtained directly from the reaction mixture by recrystallization from a suitable solvents such as methylcyclohexane.

The 3-hydroxypyrazoles formed in the process of the present invention are useful as intermediates in making active herbicidal phenoxypyrazoles. The herbicidal 3-phenoxypyrazole can be made by reacting the 3-hydroxypyrazole with a substituted halobenzene such as 4-fluoro-2-methoxycarbonylnitrobenzene with potassium carbonate in DMSO at an elevated temperature, e.g., 50° to 80° C.

The following examples are presented to illustrate various embodiments of the invention. These examples are illustrative of the novel process of the invention and do not imply any limitations as of its scope.

EXAMPLE 1

1-methyl-3-hydroxy-5-trifluoromethylpyrazole

A mixture of 33.82 g (0.20 mole) of methyl 4,4,4-trifluoro-3-amino-2-butenoate and 10.1 g (0.22 mole) of methylhydrazine was heated at 50° C. for 22.25 hr. The mixture was then cooled, and 15 ml. of water and about 12 ml. of conc. hydrochloric acid were added to bring the pH of the mixture to 6.5–7.0. The precipitated product was filtered off and dried to obtain 25.26 g (76% yield) of the product m.p. 130.5°–131° C.

EXAMPLE 2

1-methyl-3-hydroxy-5-trifluoromethylpyrazole 30.82 g (0.2 mol) of 4,4,4-trifluoro-3-amino-2-butenamide (prepared by addition of 2 equivalents of ammonia to the corresponding alkenoic ester) was added to 10.1 g (0.22 mol) of methylhydrazine at room temperature. A slight exotherm raised the temperature to 30° C. The mixture was stirred for 1 hr. at which time the mixture became semi-solid; 10 ml. of ethanol was added to improve stirring. After another 1.5 hr., 7 ml. of ethanol was added, again to aid in stirring the mixture. After a total of 24 hr., the mixture was taken up in 25 ml. of water, the pH was adjusted to 6.5–7.0 with conc. hydrochloric acid (17 ml.), and the precipitated product was collected by filtration and dried to obtain 21.37 g (65.3%) of product m.p. 129°–131° C.

EXAMPLE 3

1-methyl-3-hydroxy-5-trifluoromethylpyrazole

A 50 ml. flask equipped with mechanical stirrer and reflux condenser was charged with 19.7 g of ethyl 3-methylamino-4,4,4-trifluoro-2-butenoate and 4.8 g of methylhydrazine and heated to 50°–65° C. for 2.75 hr., then to 40°–45° C. for 2 hr., and then allowed to cool to room temperature and stand overnight. The clear reaction mixture was taken up in 15 ml. of water and conc. hydrochloric acid added dropwise to pH 6.0–6.5 which required 5.2 ml. of acid. The precipitated product was collected by filtration and dried to obtain 7.06 g (42.5%) of product m.p. 127°–128.5° C.

EXAMPLE 4

1-methyl-3-hydroxy-5-trifluoromethylpyrazole

A mixture of 17.5 g of ethyl 4,4,4-trifluoro-3-(1 pyrrolidinyl)-2-butenoate and 3.7 g of methylhydrazine was heated at 50° C. for 4.3 hr., then at 60° C. for another 25.5 hr. The mixture was then cooled, 15 ml. of water was added and the pH adjusted to 6.5–7.0 by addition of 3.1 ml. of conc. hydrochloric acid. The resulting precipitate was collected by filtration and dried to obtain 3.4 g of solid which was slurried with 6% sodium bicarbonate solution for 1 hr., then filtered and washed with water to obtain 2.67 g of product m.p. 130°–131° C.

Although this invention has been described with respect to specific embodiments, the details thereof are not to be construed as limitations, for it will be apparent that various embodiments, changes, and modifications may be resorted to without departing from the spirit and scope thereof and it is understood that such equivalent embodiments are intended to be included within the scope of this invention.

We claim:

1. A process for preparing a compound having the formula:

$$(CY_3)_nA\underset{R_3\diagdown N\diagup N}{\overline{\phantom{XXXXX}}}\overset{R_1}{\underset{OH}{\diagdown}}$$

which comprises reacting $$(CY_3)_nA\underset{NZX}{\overline{\phantom{XXX}}}\overset{O}{\underset{R_1}{\diagdown}}R_2$$

with $R_3NHNH_2$
wherein each Y is independently hydrido or halo; n is 0 or 1; A is $CFY_2$ when n is 0 and A is CFY when n is 1; Z is hydrido and X is hydrido, lower alkyl or phenyl, or Z and X together are cyclic alkyl, $R_1$ is hydrido or halo; $R_2$ is hydroxy, alkoxy, alkylthio or alkylamino; and $R_3$ is lower alkyl.

2. The process of claim 1 wherein $R_3$ is methyl and $R_1$ is hydrido.

3. The process of claim 2 wherein A is $CF_2Y$—.

4. The process of claim 3 wherein Y is hydrido or fluoro.

5. The process of claim 4 wherein Y is fluoro.

6. The process of claim 4 wherein Y is hydrido.

7. The process of claim 1 wherein Z and X are hydrido.

8. The process of claim 3 wherein $R_2$ is alkoxy.

* * * * *